United States Patent [19]

Tardy

[11] 4,341,125

[45] Jul. 27, 1982

[54] DEVICES FOR EXTRACTING A SAMPLE OF FLUID FROM A HYDRAULIC CIRCUIT

[75] Inventor: Roger Tardy, Nexon, France

[73] Assignee: Sofrance S.A., Limoges, France

[21] Appl. No.: 207,768

[22] Filed: Nov. 17, 1980

[30] Foreign Application Priority Data

Nov. 30, 1979 [FR] France .................. 79 29545

[51] Int. Cl.³ .......................................... G01N 1/14
[52] U.S. Cl. ............................. 73/863.25; 73/863.84
[58] Field of Search ........... 73/863.21, 863.23, 863.24, 73/863.25, 863.86

[56] References Cited

U.S. PATENT DOCUMENTS 3,010,583  11/1961  Kenyon ........................ 73/863.23
4,014,216   3/1977  Thornton et al. ............. 73/863.23
4,150,575   4/1979  Magorien ...................... 73/863.86

Primary Examiner—S. Clement Swisher

Attorney, Agent, or Firm—McCormick, Paulding & Huber

[57] ABSTRACT

The present invention concerns a device for extracting a sample of fluid from a hydraulic circuit having an extraction take-off, for detection of impurities.

The device comprises in particular a body (10, 12) provided with a ferrule (14), capable of fitting on the take-off; a perforator (22) fixed on the ferrule (14) and provided with at least one orifice capable of distributing the fluid into the body; a carrier (26) capable of receiving a container (32) provided with a perforatable capsule (36) and a filtering membrane (40), the carrier being displaceable from one to the other of two positions, comprising an extraction position where the capsule (36) is perforated by the perforator (22) and where the fluid penetrates into the container (32), and a non-extraction position where the capsule (36) is not perforated by the perforator (22), and where the fluid runs out outside the container (32).

11 Claims, 4 Drawing Figures

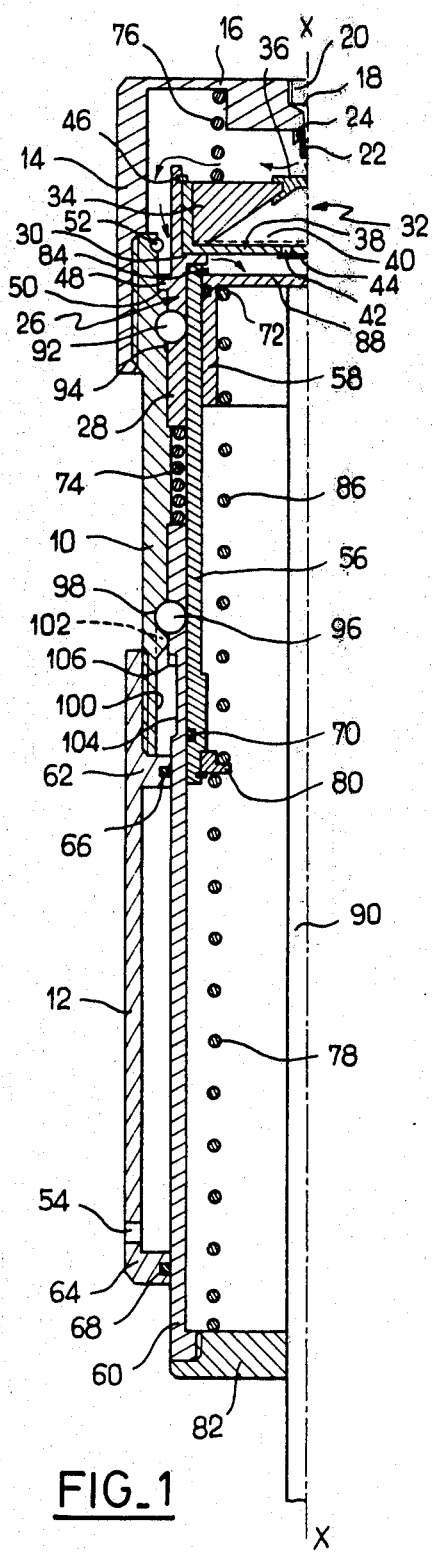
FIG_1
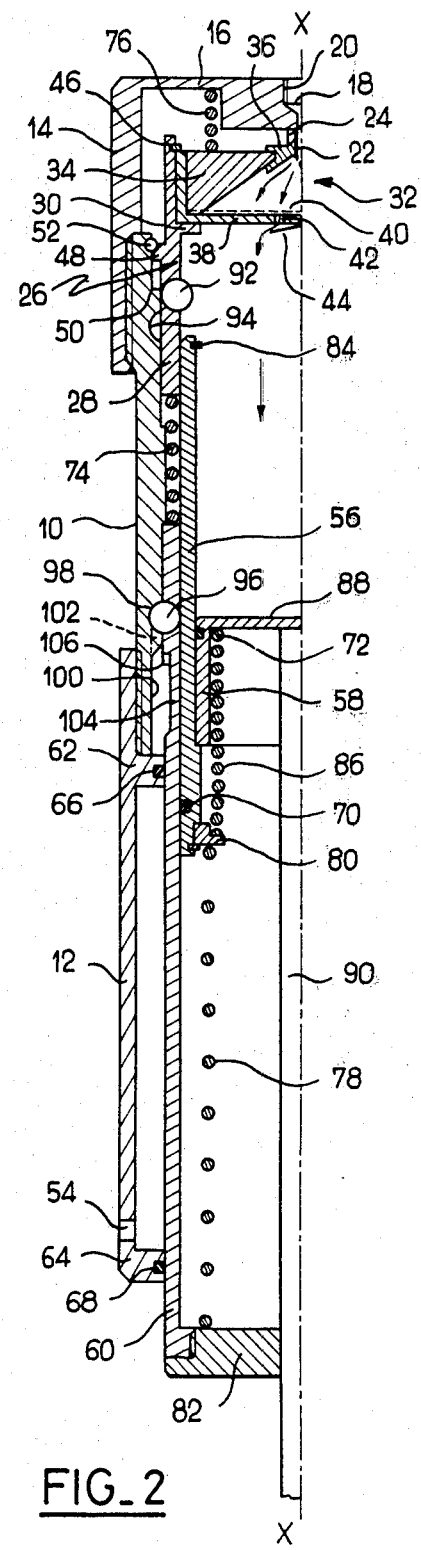
FIG_2

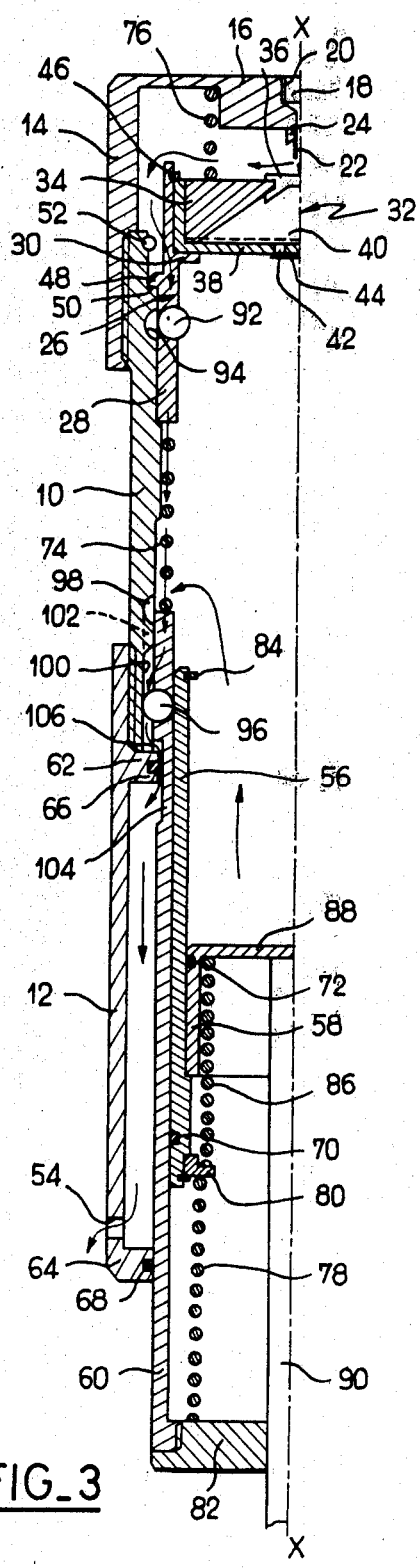
FIG_3
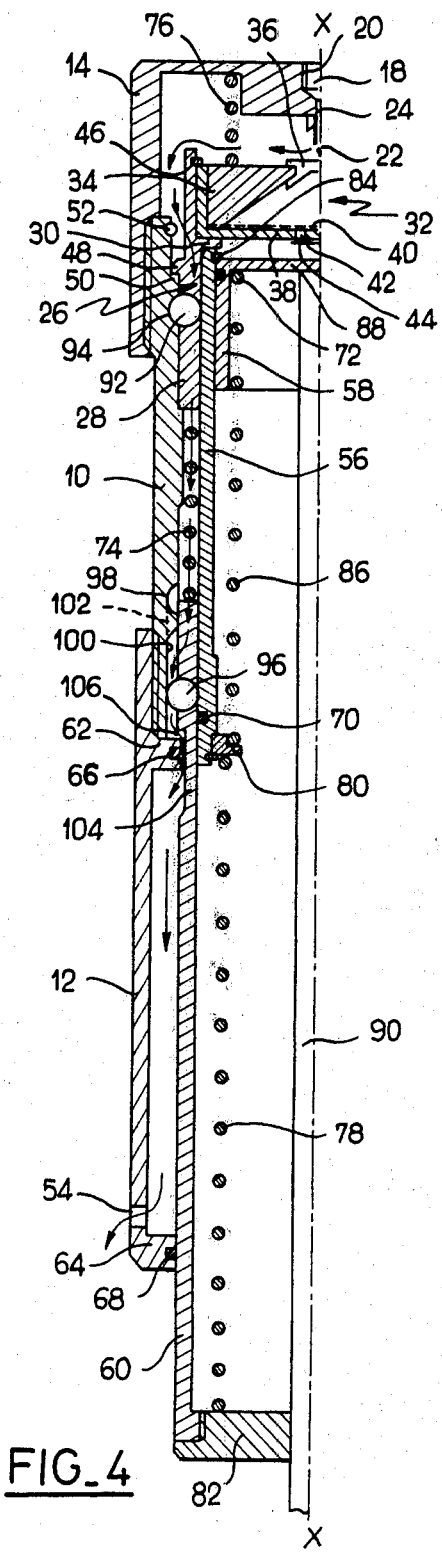
FIG_4

DEVICES FOR EXTRACTING A SAMPLE OF FLUID FROM A HYDRAULIC CIRCUIT

The present invention concerns devices for extracting a sample of fluid from a hydraulic circuit, for the purpose of detecting the presence of impurities in that circuit.

In hydraulic circuits, such as notably hydraulic control circuits, it is necessary to extract periodically samples of fluid for the purpose of detecting the presence of impurities in the circuit.

For this purpose, it is known to provide extraction take-offs on the pipes of the hydraulic circuit, intended for extracting, from within the piping itself, a representative sample of fluid to be analysed.

In that case one connects an extraction device to the take-off, one carries out a preliminary rinsing of the device by passing a certain quantity of the fluid, and then one collects a sample of the fluid for the purposes of analysis.

Then one passes this sample through a filtering membrane with pores which are of known shapes and dimensions, one rinses the membrane and possibly dries it, and finally one counts the particles deposited on the membrane.

The devices existing at present for making such extractions present certain inconveniences, arising particularly from the fact that there are dead zones during the rinsing, and that these devices include components which are in movement during the sampling operations, thus giving rise to risks of retention of impurities.

The present invention relates particularly to elimination of the inconveniences mentioned above, by producing a device for extraction of a sample of fluid from a hydraulic circuit having an extraction take-off, in which there do not exist any dead zones during the rinsing, and in which the movable components become stationary during the sampling operations.

The present invention concerns more paticularly a device for extraction of a sample of fluid from a hydraulic circuit having an extraction take-off, comprising:

a body provided with a ferrule which can be fitted on the take-off;

a perforator fixed to the ferrule and provided with at least one orifice capable of distributing the fluid into the body;

a container provided with a perforatable capsule and a filtering membrane;

a movable carrier capable of receiving the container, the carrier being displaceable from one to the other of two positions, comprising an extraction position where the capsule is perforated by the perforator and where the fluid penetrates into the container, and a non-extraction position where the capsule is not perforated by the perforator, and where the fluid flows outside the container;

first resilient return means tending to return the carrier towards the extraction position;

second resilient return means, of lesser force than the first resilient return means, tending to return the carrier towards the non-extraction position;

means for immobilising the carrier in the non-extraction position;

first releasing means capable of releasing the immobilising means;

second releasing means capable of releasing the first resilient return means; and means defining a space and capable of: receiving a first predetermined volume of fluid, namely a rinsing volume, while the carrier is in the non-extraction position; operating the first releasing means and thus causing the displacement of the carrier towards the extraction position, receiving a second predetermined volume of fluid, namely a sample volume, which passes through the filtering membrane of the container; operating the second releasing means and thus causing the displacement of the carrier towards the non-extraction position; and discharging outside the body the fluid coming from the perforator and the fluid rejected from the space.

According to one preferred feature of the invention, the means defining a space are constituted by at least one piston sliding axially in the interior of an annular portion of the carrier, which itself slides axially in the interior of the body, and a sleeve is mounted for sealed axial sliding in a portion of the annular space contained between the body and the piston.

According to another preferred feature of the invention, the first resilient return means are constituted by a compression spring confined in the portion of the annular space contained between the body and the piston.

According to another preferred feature of the invention, the second resilient return means are constituted by a compression spring confined between the ferrule and the carrier by abutting the container.

According to another preferred feature of the invention, the means for immobilising the carrier are constituted by a set of balls displaceable radially in seats in the carrier and capable of cooperating with an annular groove in the body, and the first releasing means are constituted by the piston.

According to another preferred feature of the invention, the second releasing means are constituted by a set of balls displaceable radially in seats in the sleeve and capable of cooperating with an annular groove in the body.

In a preferred form of embodiment of the invention, the means defining the space are constituted by two pistons, one of which slides within the other between two extreme positions, the two pistons being urged back resiliently in the direction of the carrier.

The devices according to the invention enable one to achieve successively a rinsing of the device by letting flow away a certain volume of fluid, the extraction of the sample without risk of introduction of parasitic pollution, and the passage of the sample through the filtering membrane at the time of extraction.

The devices according to the invention also enable one to achieve rinsing and drying of the membrane to remove the traces of the fluid extracted, and to fix the particles on the membrane, as will be explained later.

The devices according to the invention have notably the following principal advantages:

the device enables one to carry out extractions on hydraulic circuits while they are working.

the rinsing before the taking of the sample occurs automatically without human intervention. The rinsing volume is constant and guarantees a representative sample of the fluid in the circuit. This operation is thus no longer left to the initiative of the operator.

the rinsing of the totality of the circuit upstream of the filtering membrane is ensured without leaving any dead zone.

after opening of the extraction take-off, that is to say from the rinsing operation up to the end of operations, the circuit upstream of the filtering membrane does not contain any component which is moving and a generator of pollution.

the start of the sampling is brought about automatically when the rinsing operation is finished.

the sample traverses the filtering membrane simultaneously with its extraction, so guaranteeing the absence of parasitic pollution.

the end of the taking of the sample occurs when the necessary and exact volume of fluid has traversed the membrane.

the operation of rinsing and of drying of the membrane can be brought about by passage of fluids such as petroleum ether and air while placing a further filtering membrane at the entrance to the device for taking a sample, so that the rinsing and drying fluids do not introduce any supplementary pollution.

the conveyance of the membrane to the testing laboratory can be carried out without risk of pollution, because it remains in the interior of its sealed container.

Other preferred features and advantages of the invention will be better understood from reading the description which will follow and which refers to the accompanying drawings, given simply by way of illustration, and in which:

FIGS. 1 to 4 represent an axial half-section of an extracting device according to the invention, in the course of four successive phases of working.

There has been shown in FIGS. 1 to 4 a device according to the invention comprising a generally cylindrical body with an axis X—X and composed of two parts 10 and 12 screwed one on another, and a ferrule 14 screwed on the part 10. The ferrule 14 includes a flat portion 16 provided with an axial bore 18 having an internal thread 20 capable of cooperating with the external thread of an extraction take-off (not shown) fixed to a circulating pipe for hydraulic fluid. Such a take-off is made in known manner, and enables one to extract the fluid from within the pipe itself, in such a way as to obtain a representative sample of the hydraulic fluid. Such a take-off likewise includes a tap to permit one to start and stop the extraction of fluid at will.

The bore 20 leads to a perforator 22 constituted by a hollow needle with a lateral outlet, the axis of which is directed along the axis X—X of the device. This perforator is surrounded by a sealing device 24 of annular shape, the function of which will be explained later.

The device also comprises a movable carrier 26 having an annular portion 28 capable of sliding in the interior of the part 10 of the body of the device. The carrier 26 has an annular internal flange 30 serving to receive a removable sealed container 32 comprising a cover 34 provided with a perforatable capsule 36, made for example of an elastomer. The container also includes a circular bottom 38 the outside of which is to abut against the flange 30 of the carrier 26 and the inside of which is provided with annular, concentric grooves and with radial channels (not shown) and can receive a filtering membrane 40 with pores which are of known shapes and dimensions. The base is provided with at least one orifice 42 through it, provided with a non-return device 44. The container is held in place in the striker 26 by means of a circlip 46.

The carrier is displaceable axially relatively to the part 10 of the body from one to the other of two positions, comprising an extraction position where the capsule 36 is perforated by the perforator 22 and where the fluid then penetrates into the container, and a non-extraction position where the capsule is not perforated by the perforator, and where the fluid flows outside the container. For this purpose, the carrier 26 is provided with an annular external flange 48 capable of abutting respectively with an annular shoulder 50 of the part 10 (non-extraction position) and an annular internal ring 52 received in an annular internal groove of the part 10 (extraction position).

The carrier 26 is furthermore provided with radial slots (not shown) permitting the fluid to be passed beneath the container, in the non-extraction position, and longitudinal slots permitting discharge of the fluid towards the exterior, in certain phases of working, the part 12 being provided for this purpose with at least one lateral opening, such as 54.

It will be noted that, in the extraction position, the container 32 ensures a uniform distribution of the discharge of fluid onto the filtering membrane 40.

The device also comprises means defining a space, constituted by at least one piston sliding axially in the interior of the annular portion 28 of the carrier 26. In the embodiment shown in the accompanying Figures, these means comprise two pistons, that is to say an outer hollow piston 56 which slides in the interior of the annular portion 28, and an inner piston 58 which slides in the interior of the outer piston 56.

The device also comprises a sleeve 60 mounted to slide sealingly in a portion of the annular space contained between the parts 10 and 12 of the body of the device and the outer piston 56. For this purpose, the part 12 has two annular internal flanges 62 and 64, respectively provided with grooves 66 and 68 each capable of receiving a sealing ring. The outer piston 56 slides in a sealed manner in the interior of the sleeve 60 thanks to a groove 70 capable of receiving a sealing ring, and the inner piston 58 slides in a sealing manner in the interior of the outer piston 56 thanks to a groove 72 capable of receiving a sealing ring.

The device also comprises first resilient return means tending to return the carrier towards the extraction position, these first means being constituted by a helical compression spring 74 confined in the portion of the annular space contained between the part 10 and the piston 56 and between the carrier 26 and the sleeve 60.

The device also comprises second resilient return means tending to return the carrier towards the non-extraction position, these second means being constituted by a helical compression spring 76, of a lesser force than the spring 74, confined between the ferrule 14 and the carrier 26 by abutting the cover 34 of the container 32.

The displacement of the piston 56 in the interior of the sleeve and of the carrier is limited by the internal flange 30 of the carrier. This piston is moreover subjected to the action of a helical compression spring 78 placed between a ring 80 fixed to the piston 56, and a bottom 82 screwed onto the lower part of the sleeve 60.

The displacement of the inner piston 58 into the interior of the outer piston 56 is limited upwards by a circlip 84 fixed to the outer piston 56. The inner piston 58 is urged upwards in the direction of the carrier by means of a helical compression spring 86 abutting against the bottom 88 of the inner piston and against the ring 80. A control rod 90 directed along the axis of the device is fixed firmly to the bottom 88 of the inner piston, and passes through the bottom 82 of the sleeve 60.

The device also comprises means for immobilising the carrier 26 in the non-extraction position. These means are constituted by a set of balls such as 92, for example four balls uniformly spaced, displaceable radially in seats made through the entire thickness of the wall of the portion 28 of the carrier 26 and capable of cooperating with an annular groove 94 in the part 10 of the body. The balls are each placed in seats made in such a way that they cannot leave their respective seat and that, when the outer piston 56 is no longer in contact with the balls, the latter tend to leave the annular groove 94 of the part 10 under the action of the force exerted by the spring 74. The outer piston thus constitutes releasing means capable of liberating the immobilising means constituted by the balls previously mentioned.

The device also comprises second releasing means capable of releasing the first resilient return means (spring 74). These second releasing means are constituted by a set of balls 96, for example four balls uniformly spaced, placed in seats in the sleeve 60 analogous to the seats previously mentioned in the carrier, and capable of cooperating with an annular groove 98 in the part 10. The balls 96 cannot leave their respective seats, but can leave the groove 98 to reach a zone 100 situated at the end of the part 10 adjacent to the flange 62 of the part 12, the internal diameter of which corresponds to the internal diameter of the groove 98, when the piston 56 has released them.

The sleeve 60 comprises also a zone 104 of reduced external diameter which, when it is opposite the flange 62 of the part 10, permits the passage of fluid towards the orifice 54 made in the part 12.

The working of the device will now be described below.

The filtering membrane 40 serving to retain the impurities contained in the sample to be extracted is placed in the interior of the container 32 and the latter is provided with its cover 34 having the perforatable capsule 36.

The container 32 is placed in the interior of the body from which one has first removed the ferrule 14, the carrier 26 being in non-extraction position. One then screws the ferrule 14 up again and then one connects the latter to the extraction take-off on the piping. After opening of the extraction take-off, the fluid enters into the device via the perforated needle 22, and it then passes into the radial slots made in the carrier 26 and arrives beneath the container 32 (FIG. 1). The pressure of the fluid acts on the inner piston 58, which descends, under the action of the fluid, while compressing the spring 86. The inner piston 58 abuts against the outer piston 56, which is then also driven and compresses the spring 78.

During its descent, the piston 56 releases the set of balls 92. At this moment, the rinsing operation is stopped and the sampling starts.

The carrier 26, under the action of the spring 74, is driven towards the perforated needle 22, taking with it the container 32, and causing the perforation of the capsule 36 by the hollow needle 22. The device 24 then ensures a perfect tightness between the needle 22 and the capsule 36. During this operation, the spring 76 is compressed by the spring 74 (FIG. 2).

The fluid then passes into the interior of the container and passes through the filtering membrane 40. The outer piston 56 continues its descent, and detects the volume which passes through the membrane. When the necessary volume is reached, the outer piston releases the set of balls 96 (FIG. 3).

As the sleeve 60 is not supported any more, it falls relatively to the part 12 of the body until its flange 106 abuts against the outer flange 62. The spring 74 is no more compressed, and the carrier 26, under the action of the spring 76, then terminates the sampling operation.

The perforated needle 22 is withdrawn from the container 32, hence the fluid does not pass any more through the membrane 36. The annular spaces contained between the parts 10 and 12 on the one hand and the piston 56 and the sleeve 60 on the other hand, communicate through slots made in the carrier 26 and the sleeve 60, as indicated by the arrows in FIG. 4.

The pistons 56 and 58 rise again under the action respectively of the springs 78 and 86. The fluid displaced by the pistons 56 and 58 is discharged to the exterior via the orifice 54 in the part 12 of the body.

When the pistons 56 and 58 reach the FIG. 4 position, the extraction operation is ended, and one can close the extraction take-off in the piping.

The device can be re-set for a further cycle of operations as described above, by pushing and turning the sleeve 60. The balls 96 then return from the zone 100 to the groove 98 thanks to longitudinal grooves such as 102 made in the inner wall of the part 10 between the groove 98 and the zone 100. The number and the spacing of the grooves 102 corresponds to the number and the spacing of the balls 96. Then the sleeve can be locked by exerting a rotation on the sleeve so that the balls 96 are no more opposite to the grooves 102. This operation causes the compression of the spring 74, which is ready for the next cycle of movements of the carrier 26.

If one wants to carry out a rinsing and drying operation, it is necessary to put in place a further filtering membrane upstream of the bore 18, and to re-set the device as described above. On pulling on the rod 90, one can simulate an extraction by drawing in the rinsing fluid through the bore 18, thanks to the suction created by the pistons 56 and 58. A cycle of movements of the carrier 26 takes place, and the passage of the filtered fluid through the container 32 causes a flushing and a rinsing of the container and of the filtering membrane, so as to apply the particles on the latter in a layer. Pulling on the rod 90 should be continued until release of the set of balls 96.

To cause the drying of the filtering membrane, one can re-start the operations above, using air.

When these rinsing and drying operations are ended, one removes the container 32, with unscrewing of the ferrule 14, and one puts in a new container in place. The container thus removed is transmitted to the laboratory for the counting of the particles retained on the filtering membrane.

The invention is not limited to the embodiment particularly described and shown with reference to the accompanying drawings, and one can imagine other embodiments without going outside the scope of the invention. Thus for example the sequences may be controlled electrically.

The means defining the volume can be constituted by a chamber defining a fixed volume instead of being constituted by two pistons. These means can also be constituted by a single piston.

One can moreover provide means for regulating the extraction volume and the rinsing volume, by adjusting the positions of the annular grooves 94 and 98 intended to cooperate respectively with the sets of balls 94 and 96. These annular grooves could for this purpose be carried by displaceable sleeves.

The devices according to the invention find a general application to the extraction of a sample of fluid in a hydraulic circuit for the purpose of detecting impurities in it. The sample is collected following an automatic working sequence, and deposits its particles on a filtering membrane, the counting of the particles being carried out later in the laboratory.

I claim:

1. A device for extraction of a sample of fluid from a hydraulic circuit having an extraction take-off, comprising:
   a body provided with a ferrule which can be fitted on the take-off;
   a perforator fixed to the ferrule and provided with at least one orifice capable of distributing the fluid into the body;
   a container provided with a perforatable capsule and a filtering membrane;
   a movable carrier capable of receiving the container, the carrier being displaceable from one to the other of two positions, comprising an extraction position where the capsule is perforated by the perforator and where the fluid penetrates into the container, and a non-extraction position where the capsule is not perforated by the perforator, and where the fluid flows outside the container;
   first resilient return means tending to return the carrier towards the extraction position;
   second resilient return means, of lesser force that the first resilient return means, tending to return the carrier towards the non-extraction position;
   means for immobilising the carrier in the non-extraction position;
   first releasing means capable of releasing the immobilising means;
   second releasing means capable of releasing the first resilient return means; and
   means defining a space and capable of: receiving a first predetermined volume of fluid, namely a rinsing volume, while the carrier is in the non-extraction position; operating the first releasing means and thus causing the displacement of the carrier towards the extraction position, receiving a second predetermined volume of fluid, namely a sample volume, which passes through the filtering membrane of the container; operating the second releasing means and thus causing the displacement of the carrier towards the non-extraction position; and discharging outside the body the fluid coming from the perforator and the fluid rejected from the space.

2. A device according to claim 1, in which the perforator is constituted by a hollow needle with a lateral outlet.

3. A device according to claim 1 or claim 2, in which the perforator is surrounded by a sealing device capable of cooperating with the perforatable capsule of the container when the carrier is in extraction position.

4. A device according to claim 1, in which the container has a circular bottom capable of receiving the filtering membrane, the bottom being provided on the inside with annular, concentric recesses and with radial channels, and being provided with at least one orifice through it, equipped with a non-return device preventing all access of fluid towards the interior of the container.

5. A device according to claim 1, in which the means defining a space are constituted by at least one piston sliding axially in the interior of an annular portion of the carrier, which itself slides axially in the interior of the body, and a sleeve is mounted for sealed axial sliding in a portion of the annular space contained between the body and the piston.

6. A device according to claim 5, in which the first resilient return means are constituted by a compression spring confined in the portion of the annular space contained between the body and the piston.

7. A device according to claim 5 or claim 6, in which the second resilient return means are constituted by a compression spring confined between the ferrule and the carrier by abutting the container.

8. A device according to claim 5, in which the means for immobilising the carrier are constituted by a set of balls displaceable radially in seats in the carrier and capable of cooperating with an annular groove in the body, and the first releasing means are constituted by the piston.

9. A device according to claim 5, in which the second releasing means are constituted by a set of balls displaceable radially in seats in the sleeve and capable of cooperating with an annular groove in the body.

10. A device according to claim 5, in which the means defining the space are constituted by two pistons, one of which slides within the other between two extreme positions, the two pistons being urged back resiliently in the direction of the carrier.

11. A device according to claim 10, in which the piston which slides in the other is provided with an axial control rod permitting one to achieve manual extraction of fluid by suction.

* * * * *